United States Patent
De Vries et al.

(10) Patent No.: US 6,262,280 B1
(45) Date of Patent: Jul. 17, 2001

(54) SHILOV-TYPE REACTIONS

(75) Inventors: Nadine Henriette Caroline De Vries, Wilmington; Donald Irwin Garnett, Hockessin, both of DE (US); David Lincoln Thorn, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/481,993

(22) Filed: Jan. 11, 2000

Related U.S. Application Data
(60) Provisional application No. 60/116,458, filed on Jan. 20, 1999.

(51) Int. Cl.⁷ .................................................. C07D 307/02
(52) U.S. Cl. ............................ 549/509; 549/506; 549/505
(58) Field of Search ..................................... 549/509, 506, 549/505

(56) References Cited

U.S. PATENT DOCUMENTS

| | | | | |
|---|---|---|---|---|
| 4,136,099 | * | 1/1979 | Smith | 549/509 |
| 5,872,266 | * | 2/1999 | Nitobe et al. | 549/429 |
| 5,917,061 | * | 6/1999 | Chen et al. | 549/509 |
| 6,147,233 | * | 11/2000 | Beavers | 549/508 |
| 6,169,189 | * | 1/2001 | Fischer et al. | 549/429 |

OTHER PUBLICATIONS

Stahl, Shannon S. et al., Homogeneous Oxidation of Alkanes by Electrophilic Late Transition Metals, *Angew. Chem. Int. Ed.*, 37, 2180–2192, 1998.

Freund, Michael S. et al., Electrocatalytic functionalization of alkanes using aqueous platinum salts, *Journal of Molecular Catalysis*, Elsevier Science B.V., 0304–5102, 1994.

Basickes, Naomi et al., Platinum(II) Mediated Oxidation of Remote C–H Bonds in Functionalized Organic Molecules, *Polyhedron*, 14, 197–202, 1994.

Labinger, Jay A. et al., Oxidation of Hydrocarbons by Aqueous Platinum Salts: Mechanism and Selectivity, *Organometallics*, 12, 895–905, 1993.

* cited by examiner

*Primary Examiner*—Deborah C. Lambkin

(57) ABSTRACT

The functionalization of compounds containing carbon-hydrogen bonds utilizing platinum compounds in Shilov-type reactions is improved by using hydrogen peroxide or selected Pt[IV] compounds as an oxidant.

18 Claims, No Drawings

SHILOV-TYPE REACTIONS

This application claims the benefit of 60/116,458 Jan. 20, 1999.

FIELD OF THE INVENTION

The functionalization of compounds containing carbon-hydrogen bonds utilizing platinum compounds in Shilov-type reactions is improved by using hydrogen peroxide or selected Pt[IV] compounds as an oxidant. The products of the various processes are useful in many ways, for example as chemical intermediates, solvents, and as monomers for polymers.

BACKGROUND OF THE INVENTION

The conversion of carbon-hydrogen bonds, especially unactivated carbon-hydrogen bonds, into other functional groups in organic compounds has always been a difficult challenge for chemists, and few methods for doing this which are selective and/or well controlled have been developed. One of these methods is the so-called Shilov-type reaction, which classically involves the combined use of a Pt[II] compound such as $PtCl_2$ and a Pt[IV] compound, almost always the $PtCl_6^{-2}$ anion, especially to create oxygen functional compounds, see for instance A. E. Shilov, et al., Coordination Chemistry Reviews, vol. 24, p. 97–143 (1977); L-C. Kao, et al., J. Chem. Soc., Chem. Commun., 1991, p. 1242–1243; A. C. Hutson, et al., J. Organometal. Chem., vol. 504, p. 69–74 (1995); G. A. Luinstra, et al., J. Organometal. Chem., vol. 504, p. 75–91 (1995); L. Wang, et al., J. Mol. Catal. A, vol. 116, p. 269–275 (1997); A. E. Shilov, *Activation of Saturated Hydrocarbons by Transition Metal Complexes*, D. Reidel Publishing Co., Dordrecht (1984); A. E. Shilov, et al., Chem. Rev., vol. 97, p. 2879–2932 (1997); and S. S. Stahl, et al., J. Am. Chem. Soc., vol. 118, p. 5961–5976 (1996). However, this reaction has two major disadvantages, namely it is not often as selective as desired, for example organic chlorine compounds are often generated, and the expensive Pt[IV] compound must be used in stoichiometric, not catalytic, quantities. Therefore, methods for overcoming one or both of these problems would enhance the usefulness of this reaction.

The mechanism of the Shilov-type reaction is well studied, and it is believed that the Pt[IV] compound acts as an oxidant, that is when the organic compound is functionalized with, for example, hydroxyl group, the organic compound is oxidized, and the Pt[IV] is the oxidant. It has been suggested by a number of authors, see for instance S. S. Stahl, et al., Angew. Chem. Int. Ed., vol. 37, p. 2180–2192 (1998), that the use of a cheaper oxidant would make the Shilov reaction more attractive, but such an oxidant has not been found. It has been pointed out that when Pt[IV] acts as an oxidizing agent it becomes Pt[II], which is one of the reactants. Numerous attempts have also been made to diminish the by-products associated with the Shilov reaction, especially the chlorinated organic by-products, but these attempts have been only partially successful.

N. Basickes, et al., Polyhedron, vol. 14, p. 197–202(1995) describes the synthesis of tetrahydrofuran and butanediols from 1-butanol using a platinum catalyst system. No mention is made of making 3-methyltetrahydrofuran.

M. S. Freund, et al., J. of Mol. Catal., vol. 87, p. L11–L15 (1994), use electrochemical methods to oxidize p-toluenesulfonic acid in the presence of a Pt[II] compound. J. A. Labinger, et al., Organometallics, vol. 12, p. 895–905 (1993) report on the use of phosphomolybdic acid or peroxydisulfate anion as an oxidant in the oxidation of p-toluenesulfonic acid in the presence of Pt[II]. No mention is made of hydrogen peroxide in either of these references.

What are needed are improved Shilov-type processes that do not have the disadvantages and/or deficiencies inherent in the prior art.

SUMMARY OF THE INVENTION

This invention discloses an improved Shilov-type process utilizing platinum salts for producing functionalized organic compounds, wherein the improvement comprises, using at a pH of about 2.0 or less, hydrogen peroxide as an oxidant.

Also disclosed in this invention is an improved Shilov-type process for producing functionalized organic compounds, using a Pt[II] salt and an oxidant which is a Pt[IV] salt, wherein the improvement comprises, using as said Pt[IV] salt $PtCl_3X \cdot Q_n$, $PtCl_4 \cdot Q_n$ or $APtCl_5 \cdot Q_n$, wherein Q is a neutral molecule which may coordinate to the Pt atom, n is zero, 1, 2 or 3, X is a monovalent anion, and A is a monovalent cation.

Another disclosure of this invention concerns a process for the production of 3-methyltetrahydrofuran, comprising: contacting at a temperature of about 0° C. to about 400° C., a compound selected from the group consisting of 2-methylbutane, 3-methyl-1-butanol and 2-methyl-1-butanol, or a mixture thereof, a Pt[II] salt, and a suitable oxidant.

A further disclosure of the present invention is a process for the simultaneous production of tetrahydrofuran and 3-methyltetrahydrofuran, comprising: contacting, at a temperature from about 0° C. to about 400° C., a mixture of n-butanol and one or both of 3-methyl-1-butanol and 2-methyl-1-butanol, in the presence of a Pt[II] compound and a suitable oxidant.

DETAILED DESCRIPTION OF THE INVENTION

Unless otherwise noted, all of the general description of the Shilov-type reactions apply to all four processes above. Herein, Roman numbers in brackets, refer to the oxidation state of a metal such as Pt.

One of the ingredients in a Shilov-type reaction is an organic compound containing at least one hydrogen bound to carbon, and preferably that carbon atom is a saturated carbon atom. In the Shilov-type reaction at least one of those hydrogen atoms is converted to a functional group, preferably an oxygen containing functional group such as a hydroxyl group, or in some cases an ether group. Sometimes the oxygen functional group is further oxidized to an oxo (keto) group, an aldehyde or a carboxylic acid.

The organic compound to be functionalized may simply be a hydrocarbon such as an alkane, but the organic compound may also initially contain one or more other functional groups. In the Shilov-type reaction such an organic compound is further functionalized. In some instances one or more of the functional groups already present may take part in the reaction. For example, as reported herein, 3-methyl-1-butanol reacts in the Shilov-type reaction to form 3-methyltetrahydrofuran, whose formation may be rationalized (although not necessarily the actual mechanism) by the initial formation of 2-methyl-1,4-butanediol, and subsequent cyclization to form the tetrahydrofuran ring.

Typically the source of the oxygen atom for the functionalized organic compound is water, so it is preferred that at least some water be present in the Shilov-type reaction. This water may be added as one of the ingredients, or in some cases, may be generated during the oxidation. The water may also be added in the form of a hydrate, such as a hydrate of one or more Pt compounds. The presence of water also often helps to dissolve some of the other reaction ingredients such as the Pt compound(s), and this is also often advantageous.

One of ingredients necessary for the Shilov-type reaction is a Pt[II] compound or salt. This may be added directly to the reaction or may be formed in situ, as by the reduction of higher valent Pt, such as Pt[IV]. Although a number of different Pt[II] compounds are useful in the Shilov-type reaction, some of the most commonly used Pt compounds are $PtCl_2$ and its hydrate, or an alkali metal salt (or its hydrate) of the $PtCl_4^{-2}$ anion, and these Pt[II] compounds are preferred herein. Since the Pt[II] compound acts in a catalytic way, its concentration in the reaction is not critical, and the typical amounts used in Shilov reactions are applicable herein.

In the first and second processes herein other process conditions useful for Shilov-type reactions may be employed, and these are known in the art, see for instance many of the references listed in the "Background of the Invention" section above; the contents of which are incorporated herein. These include such conditions as temperature, process media, and reactant concentrations.

In the first process hydrogen peroxide is used as an oxidant. It is generally agreed upon that Pt[IV] compounds act as oxidants in Shilov-type reactions, and they are needed in stoichiometric quantities (compared to the organic compound substrate), which makes the process very expensive to run. Hydrogen peroxide may be used as the oxidant at pH's of about 2.0 or less, preferably about 1.0 or less. If the process solution contains about 25 or more volume percent of water, the pH may be measured directly by using a standard pH meter (glass electrode). If the process solution contains more than one phase, the phase containing the greater amount of water should be measured. If the process medium does not contain about 25 or more volume percent water, then distilled water should be added until it is 25 volume percent water and the pH measured as above.

In the first process (Bronsted) acids may be added to obtain the correct pH, about 2.0 or less. Any strong acid (strong enough to produce the desired pH) may be used, such as trifluoromethanesulfonic acid (triflic acid), other sulfonic acids provided that any attached hydrocarbon groups do not significantly interfere with the Shilov-type reaction, hexafluorophosphoric acid, hexafluoroantimonic acid, tetrafluoroboric acid and sulfuric acid. An acid whose anions are weakly coordinating, such as triflic acid, hexafluorophosphoric acid, hexafluoroantimonic acid, and tetrafluoroboric acid are also preferred. Weakly coordinating (sometimes also called noncoordinating) anions are known in the art, see for instance W. Beck., et al., Chem. Rev., vol. 88, p. 1405–1421 (1988), and S. H. Strauss, Chem. Rev., vol. 93, p. 927–942 (1993).

In the first process the hydrogen peroxide is required in stoichiometric quantities, and may, for maximum efficiency, be required in greater than stoichiometric quantities because some of it may be ineffective as an oxidant in the Shilov-type process. In one preferred method, the hydrogen peroxide is added slowly (either continuously or in small increments) as the reaction proceeds. The hydrogen peroxide is preferably added as an aqueous solution, more preferably a solution of about 3 to about 55 percent by weight hydrogen peroxide. Such solutions are commercially available. Surprisingly the presence of hydrogen peroxide apparently does not oxidize all of the Pt[II] present, which is necessary for the Shilov-type reaction to proceed, but the hydrogen peroxide is believed nevertheless to oxidize some of the Pt[II] present to Pt[IV], thereby providing an oxidant for the Shilov-type reaction. Also the hydrogen peroxide apparently often does not significantly oxidize the organic product(s) of the process.

In the second process disclosed herein a specified Pt[IV] compound, $PtCl_3X.Q_n$, $PtCl_4.Q_n$ or $APtCl_5.Q_n$ is used. In all of these compounds it is preferred that Q, if present, is water ($H_2O$). X is a monovalent anion. It is preferred that X is triflate, other sulfonates which do not contain any attached hydrocarbon groups or functionalized hydrocarbon groups that significantly interfere with the Shilov-type reaction, hexafluorophosphate, hexafluoroantimonate, tetrafluoroborate, hydrogen sulfate, nitrate, or noncoordinating chloride, and that A is an alkali metal or hydrogen cation. It is especially preferred that X is triflate or noncoordinating chloride. Preferred compounds in this process are $PtCl_4.Q_n$ wherein n is 0, or n is 2 and Q is $H_2O$. In all of these compounds when n is not 0, it is preferred that it be a number such that the Pt atom is hexacoordinate. It is also preferred that Q is a ligand that is water or may be displaced by water. By "may be displaced by water" is meant that when the compound containing the ligand in question is placed in aqueous solution, the resulting Pt compound is a hydrate. The amount of $PtCl_3X.Q_n$, $PtCl_4.Q_n$ or $APtCl_5.Q_n$ used in the second process will be the same (on a molar basis) as with other Pt[IV] compounds in the Shilov-type process, such as those containing the $PtCl_6^{-2}$ anion. It is believed that this will be a stoichiometric quantity for the desired amount of organic compound to be reacted.

In the third process herein one or more of 2-methylbutane, 2-methyl-1-butanol and 3-methyl-1-butanol are reacted with a Pt[II] compound and a suitable oxidant to obtain 3-methyltetrahydrofuran. By a "suitable oxidant" is meant any oxidant which is useful in a Shilov-type process, such as Pt[IV], for example in the form of $PtCl_4$ hydrate or a compound containing the $PtCl_6^{-2}$ anion, oxygen, or hydrogen peroxide as described herein. A preferred oxidant is hydrogen peroxide, used as described in the first process herein.

The process is carried out at a temperature of about 0° C. to about 400° C., preferably about 20° C. to about 250° C., more preferably 75° C. to about 150° C. A preferred form of Pt[II] is $PtCl_2$ or any of its hydrates, or any of the alkali metal salts (including hydrates) of the $PtCl_4^{-2}$ anion. When oxygen is used as the oxidant a preferred temperature range is about 150° C. to about 375° C. Generally speaking, when higher temperatures are used (>200° C.), reaction times will usually be shortened. When 2-methylbutane is used as the substrate, enough oxidant is used to oxidize it through (presumably one or more alcohols) to 3-methyltetrahydrofuran. At lower temperatures it is preferred that the process be carried out in the liquid phase.

The ratios of ingredients in the third process is not critical, since the Pt[II] is catalytic in nature. The amount of oxidant present will determine, to some extent, how much of the desired product, 3-methyltetrahydrofuran, will be produced. Since some of the oxidant added may not be effective, it may advantageous to add excess (more than the stoichiometric amount) of oxidant. A molar ratio of oxidant:organic substrate of 0.05 to 20 is a useful range, preferably provided that sufficient oxidant is present to prevent formation of metallic platinum during the course of the process, as it is well known that metallic platinum causes the formation of products other than the usual products of the Shilov-type reaction, see for example A. C. Hutson, et al., J. Organometal. Chem., vol. 504, p. 69–74 (1995). As noted above, if hydrogen peroxide is used as the oxidant it is preferable to add it while the process is taking place, either continuously or in small increments.

It is preferred to carry out the third process in the presence of water. However it is noted that in the third process water is produced by the formation of the tetrahydrofuran ring, so not much water may be required initially.

In a fourth process, n-butanol and one or both of 2-methyl-1-butanol and 3-methyl-1-butanol are reacted with a Pt[II] compound and a suitable oxidant to form tetrahydrofuran and 3-methyltetrahydrofuran simultaneously. By a "suitable oxidant" is meant any oxidant which is useful in a Shilov-type process, such as Pt[IV], for example in the form of $PtCl_4$ hydrate or a compound containing the $PtCl_6^{-2}$ anion, oxygen, or hydrogen peroxide as described herein. A preferred oxidant is hydrogen peroxide.

The fourth process is carried out at a temperature of about 0° C. to about 400° C., preferably about 20° C. to about 250° C., more preferably 90° C. to about 150° C. A preferred form of Pt[II] is $PtCl_2$ or any of its hydrates, or any of the alkali metal salts (including hydrates) of the $PtCl_4^{-2}$ anion. When oxygen is used as the oxidant a preferred temperature range is about 150° C. to about 375° C.

The products of the various processes are useful in many ways, for example, as chemical intermediates, solvents, and as monomers for polymers. For example, 1,3-propanediol, tetrahydrofuran and 3-methyltetrahydrofuran are useful as monomers for polyesters, the former for polyesters, and the two latter compounds for polyethers. The use of oxidants such as $PtCl_4$ is believed to often improve the rate of functionalization and/or decrease the amount of organochlorine compounds relative to the amount of alcohols or ethers formed.

In the Examples, the following abbreviations are used:

3CP—3-chloro-1-propanol
3G—1,3-propanediol
BDO—butanediol
HOTf—trifluoromethanesulfonic acid
PA—propionaldehyde
n-PrOH—n-propanol
THF—tetrahydrofuran

Comparative Example A

Comparison of $PtCl_4$ vs. $PtCl_6^{-2}$ as Oxidant

Two solutions were prepared, one with 0.168 g $PtCl_4$ (0.50 mmol), 0.023 g $Na_2PtCl_4$-hydrate (0.05 mmol), and 0.035 g n-propanol (0.58 mmol) in 1 ml $D_2O$; the second had 0.281 g $Na_2PtCl_6$-hydrate (0.50 mmol), 0.023 g $Na_2PtCl_4$-hydrate (0.05 mmol), 0.035 g n-propanol (0.58 mmol) in 1 ml $D_2O$. Both were heated for 1 hr at 100° C. (oil bath) and analyzed by NMR. (In acidic aqueous solvent the NMR spectrum of n-PrOH is 0.95 t, 1.61 pseudo sext, 3.62 t; of 3-CP is 2.05 quint, 3.75 t, 3.80 t; of 3G is 1.84 quint, 3.74 t.) The first solution had "significant" amounts of 2 major products (together on the order of ¼ of the amount of remaining n-propanol), the second solution had much less of either product (perhaps ⅒ of the amount of remaining n-propanol). The major products were identified as 3G and 3CP by comparison with added authentic compounds. In the first solution ($PtCl_4$ used as oxidant), 3G and 3CP were present in roughly equal amounts; in the second solution ($PtCl_6^{-2}$ used as oxidant), 3CP was present in greater amount than 3G.

Comparative Example B

Comparison of $PtCl_4$ vs. $PtCl_6^{-2}$ as Oxidant

Two fresh solutions similarly to the two solutions in Comparable Example A. Each was analyzed by NMR, then heated to 100° C. (oil bath) and re-analyzed by NMR after 15, 30, 45, 60, and 75 minutes. The results are shown in Table 1. Relative amounts of products are approximate and given versus the amount of n-PrOH remaining at the time. 1,2-Propanediol was also observed as a minor component in the later stages of each sample.

TABLE A

| Oxidant | Time | Appearance | Major Organic Products |
|---|---|---|---|
| $PtCl_4$ | 0 | orange mixture | n-PrOH only |
| | 15 | red-orange mixture | 3G, 3CP, each 10% of n-PrOH |
| | 30 | orange soln, black solids | 3G, 3CP, each 10% of n-PrOH, PA |
| | 45 | heavy metal deposit | similar to 30 min, maybe more PA |
| | 60 | heavy metal deposit | similar to 45 min |
| $PtCl_6^{-2}$ | 0 | orange soln | n-PrOH only |
| | 15 | 5 orange soln | mostly n-propanol, traces of others |
| | 30 | orange soln | traces of 3CP, others |
| | 45 | orange soln | 3CP, 3G, together 3% of n-PrOH |
| | 60 | orange soln | similar to 45 min, more product |
| | 75 | orange soln | 3CP (5% of n-PrOH), 3G (2% of n-PrOH) |

EXAMPLE 1

Use of Hydrogen Peroxide as Oxidant

A mixture of 0.145 g $PtCl_4$, 0.12 g HOTf, 0.058 g n-butanol in ca. 1 ml $D_2O$ was prepared and centrifuged to clarity. The solution was alternately heated (100±2° C.), analyzed by NMR spectroscopy, and monitored for visible absorbance at 450 nm (by decanting into 2 mm cell). (In acidic aqueous solvent, the NMR spectrum of n-butanol is 0.80 t, 1.24 sext, 1.43 quint, 3.51 t (all coupling constants ca. 7 Hz); of THF is 1.80 m, 3.66 m; of butane-1,3-diol is 1.10 d, 1.60 pseudo quart of d, 3.60 t, 3.87 pseudo sept.) "Pt[IV]" has a higher visible absorbance at 450 nm than does "Pt[II]" under these conditions. Results are given in Table 1. All conversions are approximate, and are calculated as the combined percent of THF and 1,3-BDO relative to the amount of n-butanol originally present.

TABLE 1

| Time. (h) | Contents | % Conversion | Absorbance |
|---|---|---|---|
| 0–1 | no products | 0 | 2.6 |
| 2.3 | trace THF, 1,3-BDO | | |
| 4.2 | THF, 1,3-BDO | 2 | |
| 4.6 | THF, 1,3-BDO | 4 | 2.4 |
| 5.0 | THF, 1,3-BDO | 8 | 1.7 |

After 5.0 h, the process was interrupted to add 1–2 small drops of 30% $H_2O_2$. The absorbance rose rapidly to 2.4. After 5.7 h (total time) the conversion was 10% and the absorbance was 1.8. Additional 30% $H_2O_2$ was added and the absorbance rose to 2.1. After 7.3 h total time the conversion was 15%. Conversions are based on the amount of n-butanol originally present.

EXAMPLE 2

3G from n-Propanol with $H_2O_2$ as the Oxidant

To a solution of 0.25 g $Na_2PtCl_4$-hydrate (Strem Chemicals, approximately tetrahydrate, ca. 0.55 mmol Pt) in 5.0 g D$_2$O was added 0.30 g HOTf and 0.354 g n-propanol (5.89 mmol), and the cloudy solution was centrifuged to clarity. About 3 ml of the solution was loaded into a 10 mm UV-VIS cell and left in the spectrometer, heated to 88–90° C. The absorbance was followed at 540 nm (at this wavelength, the absorbance of "Pt[IV]" is less than the absorbance of "Pt[II]") and was initially about 0.45. Two drops of 30% H$_2$O$_2$ (Aldrich Chemical Co., Milwaukee, Wis., USA) were added, causing rapid bleaching (red-orange to yellow) followed by rapid evolution of gas (oxygen) and lowering of absorbance to about 0.35. The absorbance gradually rose, returning to about 0.40 to 0.45 after 8 to 10 min, at which point another two drops of 30% H$_2$O$_2$ were added to oxidize the Pt population and lower the absorbance back to about 0.30 to 0.35. (The evolving gas prevented a precise absorbance reading.) This was repeated for a total of 8 additions of H$_2$O$_2$ over about 2 h whereupon the solution was analyzed by NMR. 3G was the major product; approximately 7.5% of the initial n-propanol was converted to 3G, which is about 0.8 turnover of the entire Pt population.

EXAMPLE 3

3G from n-Propanol with H$_2$O$_2$ as the Oxidant

A solution of Na$_2$PtCl$_4$-hydrate (ca. 0.55 mmol Pt), n-propanol (7.06 mmol), D$_2$O (5 g), HOTf (0.3 g), at 88–90° C. in a UV-VIS chamber was treated roughly every 10–14 minutes with ca. 2 drops 30% H$_2$O$_2$ to keep the absorbance between about 0.35 and 0.45. The absorbance range gradually lowered; after 11 such additions of H$_2$O$_2$ the absorbance range was about 0.25 to 0.35. After a total of 23 additions of H$_2$O$_2$ the experiment was interrupted and allowed to stand at room temperature overnight. The following day the solution was re-heated and periodic addition of H$_2$O$_2$ was resumed. More time was required between additions and the average absorbance seemed to rise, approaching a range of 0.3 to 0.4. After a grand total of 52 additions of H$_2$O$_2$ the solution was analyzed by NMR, revealing n-propanol, 3G, and two more compounds believed to be acetic acid and 1,2-propanediol in the approximate molar ratios 1:0.3:0.1:0.1. Using 0.55 mmol Pt and based on 7.06 mmol n-propanol initially present, the estimated final composition is 4.7 mmol n-propanol, 1.4 mmol 3G (ca. 2.5 turnovers of the Pt population), 0.5 mmol acetic acid (ca. 0.9 turnover of the Pt population), 0.5 mmol 1,2-propanediol (ca. 0.9 turnover of the Pt population). Considerably greater than one turnover of the entire platinum population was achieved and the system was still working when the reaction was stopped.

EXAMPLE 4

3G from n-Propanol with H$_2$O$_2$ as the Oxidant

A solution of PtCl$_4$ (0.498 g), Na$_2$PtCl$_4$-hydrate (0.069 g) (total Pt about 1.63 mmol), HOTf (0.48 g) in D$_2$O (ca. 3 ml) was treated with ca. 0.1 ml 30% H$_2$O$_2$ and heated until oxygen evolution slowed, then centrifuged to clarity. The solution was loaded into a jacketed vessel heated to 90–92° C. by hot water circulation through the jacket, and fitted with a dropping funnel to add 30% H$_2$O$_2$ at about 30–90 seconds per drop (with occasional bursts of 0.5–1.0 ml) and a reflux condenser. Then n-propanol (1 ml) was added. After about 7 hrs the solution was sampled for NMR, revealing considerable amounts of 3G (along with 1,2-propanediol and, presumably, acetic acid), then let cool overnight. The next day the solution was centrifuged to remove metallic Pt (which is believed to have resulted from solution coating the upper walls of the vessel during periods of foaming, followed by decomposition as a result of heating without re-oxidation), the vessel cleaned, and the reaction resumed. After 3 hrs, NMR analysis revealed more 3G, acetic acid, 1,2-propanediol. More n-propanol was then added (3 ml) and the reaction continued for 5 more hrs (total reaction time ca. 15 hrs). The solution was sampled for NMR analysis and allowed to cool without H$_2$O$_2$ addition (some Pt metal deposited during cool down). The solution was then partially evaporated and extracted with valeraldehyde (2×1 ml). By NMR analysis the valeraldehyde layer was found to contain 3G-valeraldehyde acetal in an amount consistent with the extraction of 2.2 mmol 3G from the solution, in good agreement with the direct NMR analysis which suggested 2.2 mmol 3G had been formed over the course of the experiment. (Authentic 3G-valeraldehyde-acetal was prepared separately for confirmation.) Thus the entire initial platinum population turned over roughly 1.3 times in the formation of 3G (obtained as isolated 3G-valeraldehyde-acetal) from n-propanol.

EXAMPLE 5

3-MethylTHF from Isoamyl Alcohol

A solution of 0.40 g PtCl$_4$, 3.0 g D$_2$O, 0.20 g HOTf was put into a jacketed vessel (as used in Example 4) fitted with reflux condenser and 30% H$_2$O$_2$ addition funnel (50–120 sec/drop). After the temperature in the vessel reached 90–92° C., 1.0 g of "isoamyl alcohol" (mostly 3-methyl-1-butanol; Sigma Chemical) was added and the two-phase reaction was allowed to run for 3 h. The H$_2$O$_2$ addition was discontinued, whereupon the reaction mixture gradually darkened and deposited metal within about 20 min. The mixture was cooled and allowed to stand overnight. Analysis of the organic (top) layer (CD$_2$Cl$_2$, NMR) and the aqueous (bottom) layer (NMR) both showed the presence of 3-methylTHF along with unreacted isoamyl alcohol (3-methyl-1-butanol), its isomer (2-methyl-1-butanol, also present in starting "isoamyl alcohol"), and additional unidentified compounds.

EXAMPLE 6

3-MethylTHF from Isoamyl Alcohol

A mixture of 0.25 g PtCl$_4$, 0.24 g HOTf, 5 ml isoamyl alcohol, 0.5 ml H$_2$O was prepared, making an apparently largely homogeneous solution. This was loaded into the jacketed vessel of Example 4, which was fitted with reflux and takeoff condensers, and with a 30% H$_2$O$_2$ addition (ca. 100 sec/drop, 0.5 ml/hr) funnel. The temperature was maintained at ca. 92° C. for 5 h while a slight "distillation cut" was collected. The distillate was biphasic; the top layer of distillate was sampled for NMR analysis (CD$_2$Cl$_2$), the bottom layer of distillate was sampled for NMR analysis (CD$_2$Cl$_2$ extract), and the pot-mixture was sampled (CD$_2$Cl$_2$-extract). 3-MethylTHF was apparent in both layers of distillate but not in the pot-mixture, suggesting it was removed from the pot by distillation about as rapidly as it was formed.

EXAMPLE 7

3-MethylTHF from 2-Methyl-1-butanol

A mixture of 0.04 g Na$_2$PtCl$_4$-hydrate, 0.13 g Na$_2$PtCl$_6$-hydrate, 0.017 g 2-methyl-1-butanol (Aldrich Chemical Co.) in 1 ml D$_2$O was left overnight at 100° C. (heating block, indicated; ca. 96° C. actual). Several new compounds were apparent by NMR, including 3-methylTHF as a major component (confirmed by separate analysis of authentic 3-methylTHF, 0.96 d, 1.48 d of quart, 2.03 m, 2.28 pseudo octet, 3.24 t, 3.84 m). Continued heating resulted in formation of heavy metallic precipitate and clear solution, by NMR analysis still containing 3-methylTHF but with other new unidentified products dominating.

EXAMPLE 8

Preparation of a Mixture of Tetrahydrofuran and 3-Methyl-tetrahydrofuran from a Mixture of n-Butanol and 3-Methyl-1-butanol A mixture of 0.05 g $Na_2PtCl_4$-hydrate and 0.58 g damp $PtCl_4$ in 3 ml $D_2O$ was centrifuged to clarity and the solution was separated into three 1-ml portions. To one portion was added 0.018 g n-butanol (available from Aldrich Chemical Co.). To the second portion was added 0.018 g 3-methyl-1-butanol (available from Aldrich Chemical Co.), and to the third portion was added 0.013 g n-butanol and 0.014 g 3-methyl-1-butanol (available from Aldrich Chemical Co.). Each solution was heated 25 min at 100° C. (oil bath). Analysis by NMR confirmed the presence of tetrahydrofuran and butane-1,3-diol in the first portion, 3-methyl-tetrahydrofuran in the second portion, and tetrahydrofuran, 1,3-butanediol, and 3-methyl-tetrahydrofuran in the third portion. The approximate ratio of tetrahydrofuran to unreacted n-butanol in the first portion was 0.14:1. The approximate ratio of 3-methyl-tetrahydrofuran to unreacted 3-methyl-1-butanol in the second portion was 0.15:1. The approximate ratio of tetrahydrofuran to 3-methyl-tetrahydrofuran to unreacted n-butanol in the third portion was 0.1:0.04:1.

What is claimed is:

1. An improved Shilov-type process utilizing platinum salts for producing functionalized organic compounds, wherein the improvement comprises, using, at a pH of about 2.0 or less, hydrogen peroxide as an oxidant.

2. The process as recited in claim 1 wherein said pH is about 1.0 or less.

3. The process as recited in claim 1 wherein said hydrogen peroxide is added continuously or incrementally during said process.

4. An improved Shilov-type process for producing functionalized organic compounds, using a Pt[II] salt and an oxidant which is a Pt[IV] salt, wherein the improvement comprises, using as said Pt[IV] salt $PtCl_3X.Q_n$, $PtCl_4.Q_n$ or $APtCl_5.Q_n$, wherein Q is a neutral molecule which may coordinate to the Pt atom, n is zero, 1, 2 or 3, X is a monovalent anion, and A is a monovalent cation.

5. The process as recited in claim 4 wherein said Pt[IV] salt is $PtCl_4$ or a hydrate thereof.

6. The process as recited in claim 4 wherein A is an alkali metal or hydrogen cation, X is noncoordinating chloride or trifluoromethanesulfonate, and Q is water.

7. A process for the production of 3-methyltetrahydrofuran, comprising: contacting at a temperature of about 0° C. to about 400° C., a compound selected from the group consisting of 2-methylbutane, 3-methyl-1-butanol and 2-methyl-1-butanol, or a mixture thereof, a Pt[II] salt, and a suitable oxidant.

8. The process as recited in claim 7 wherein said Pt[II] salt is $PtCl_2$ or a hydrate thereof, or an alkali metal salt of the $PtCl_4^{-2}$ anion or a hydrate thereof.

9. The process as recited in claim 7 wherein said oxidant is a Pt[IV] compound or hydrogen peroxide.

10. The process as recited in claim 7 wherein said temperature is about 75° C. to about 150° C.

11. The process as recited in claim 7 wherein said compound is selected from the group consisting of 3-methyl-1-butanol, 2-methyl-1-butanol, and a mixture thereof.

12. The process as recited in claim 10 wherein said process is carried out in the liquid phase.

13. The process as recited in claim 12 wherein said liquid phase is an aqueous phase.

14. The process as recited in claim 7 wherein one or both of butane and 1-butanol are present so that tetrahydrofuran is also formed.

15. A process for the simultaneous production of tetrahydrofuran and 3-methyltetrahydrofuran, comprising: contacting, at a temperature from about 0° C. to about 400° C., a mixture of n-butanol and one or both of 3-methyl-1-butanol and 2-methyl-1-butanol, in the presence of a Pt[II] compound and a suitable oxidant.

16. The process as recited in claim 15 wherein the temperature is from about 20° C. to about 250° C.

17. The process as recited in claim 15 wherein said Pt[II] compound is selected from the group consisting of $PtCl_2$ and hydrates thereof, alkali metal salts or hydrates thereof, alkali metal salts of $PtCl_4^{-2}$ anion or hydrates thereof.

18. The process as recited in claim 15 wherein the oxidant is hydrogen peroxide.

* * * * *

UNITED STATES PATENT AND TRADEMARK OFFICE
CERTIFICATE OF CORRECTION

PATENT NO. : 6,262,280 B1
DATED : July 17, 2001
INVENTOR(S) : De Vries, et al.

It is certified that error appears in the above-identified patent and that said Letters Patent is hereby corrected as shown below:

Column 10,
Line 13, change "or" to -- and --.
Line 43, after "thereof," (second occurrence) insert -- and --.

Signed and Sealed this

Ninth Day of October, 2001

*Attest:*

NICHOLAS P. GODICI
*Attesting Officer*    *Acting Director of the United States Patent and Trademark Office*